United States Patent [19]

Malin et al.

[11] Patent Number: 4,565,688

[45] Date of Patent: Jan. 21, 1986

[54] QUATERNIZED PHTHALOCYANIN DERIVATIVES

[75] Inventors: Michael J. Malin, Park Ridge, N.J.; Bernard Loev, Scarsdale; Deng R. Hwang, Tarrytown, both of N.Y.

[73] Assignee: Technicon Instruments Corporation, Tarrytown, N.Y.

[21] Appl. No.: 551,242

[22] Filed: Nov. 14, 1983

[51] Int. Cl.$^4$ ...................... C09B 47/04; C09B 47/30; C09B 47/32

[52] U.S. Cl. ..................................... 424/3; 260/242.2; 260/245.1; 260/245.73; 260/245.74; 260/245.76; 260/245.8; 436/63

[58] Field of Search ............ 260/242.2, 245.1, 245.73, 260/245.75, 245.76, 245.8; 424/3; 436/63

[56] References Cited

U.S. PATENT DOCUMENTS 3,210,345 10/1965 Gamlen et al. ............ 260/245.8 X
3,954,392 5/1976 Dien ................................. 260/245.8

OTHER PUBLICATIONS

Scott, J. Microscopy, vol. 119, (1979), pp. 373–381.

Primary Examiner—Richard L. Raymond
Attorney, Agent, or Firm—E. H. Gorman, Jr.; J. R. Cartiglia

[57] ABSTRACT

New phthalocyanin derivatives which can be used to differentiate basophils from other blood cells are disclosed. The compounds to which the present invention are quaternary salts of a substituted phthalocyanin structure wherein the substitutions are each independently hydrogen, sulfonate, or a $C_1$-$C_7$ hydrocarbon, optionally containing at least one heteroatom, with the proviso that at least one of them is

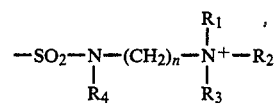

in which $R_1$-$R_3$ are each independently lower alkyls, cycloalkyls or olefins of which at least one is $C_2$-$C_4$ and two may join to form a ring; $R_4$ is hydrogen or a $C_1$-$C_3$ alkyl; n is an integer from 1 to 6; M is a polyvalent metal ion. It is preferred that at least two and especially at least three substitutions have the structure so set forth.

9 Claims, No Drawings

QUATERNIZED PHTHALOCYANIN DERIVATIVES

BACKGROUND OF THE INVENTION

1. Field of the Invention

This invention relates to the field of phthalocyanin compounds and their use as biological stains or as dyes.

2. Brief Description of the Prior Art

The differentiation of tissue and cell types by their staining properties has long been a major tool in histology and hematology. Several phthalocyanin compounds are known for use as such. The first of these to be discovered is called Alcian Blue and has the following structure:

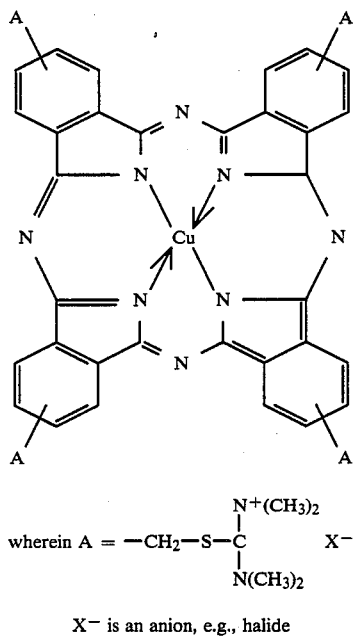

wherein A = —CH$_2$—S—C(N$^+$(CH$_3$)$_2$)(N(CH$_3$)$_2$)  X$^-$

X$^-$ is an anion, e.g., halide

Alcian Blue has been used for the differential staining of basophils. The copper phthalocyanin cationic dyes are not sufficiently specific to achieve the selective staining of basophils when used alone because they also stain other cells which possess polynucleotides, e.g., DNA and RNA. In addition, basophils stain because of the unique presence in them of heparin, a sulfated polysaccharide. One way of establishing the desired selectivity is to combine it with lanthanum chloride which masks the polynucleotide phosphate groups and thereby prevents them from binding the phthalocyanin anion.

The use of Alcian Blue requires a closely controlled, highly acidic pH and it is heat labile. At alkaline pH and when exposed to heat, Alcian Blue forms particulates (insoluble dyes). This tendency to precipitate has been a longstanding problem in Alcian Blue-containing reagents. Automated analysis instruments contain components such as filters which collect these precipitates. This can interfere with the reliability of the determinations being made and even the operation of instruments on which this method is performed. It has nonetheless been considered the dye of choice because of its specificity and distinct color. For more background information on Alcian Blue, see Gilbert, et al, Basophil Counting With A New Staining Method Using Alcian Bue, Blood, 46: 279-286 (1975).

Other phthalocyanin dyes have since been developed. For example, Bloom, et al, Histochemie, 2: 48-57 (1960) shows the use of underivatized Astra Blue (free base) to stain biological tissues containing mucopolysaccharides, particularly mast cells. The Astra Blue free base is used at pH 0.2-0.3, which gives it a positive charge. The low pH allows selectivity because of the inherent strength of sulfuric acid derivatives, e.g., heparin, which is ionized at pH 0.3, as compared to the weakness of phosphoric acid derivatives, e.g., DNA, which is not ionized at pH 3.0.

Inagaki, Acta Hematologica Japonica, 32(4): 642-647 (1969), describes for staining basophil and mast cell granules using free base Astra Blue and a fixative solution of Acridine Orange in methanol (pH about 0.3). Inagaki examined saturated cetyl pyridinium chloride in absolute methanol and saturated Acridine in absolute methanol for the fixation of peripheral blood and bone marrow smears. Cetyl pyridinium chloride securely preserved the basophil granules and the mast cell granules, but the Astra Blue staining tended to be prevented. Acridine could not preserve these cell granules sufficiently in the above described procedure.

Scott, *The Molecular Biology Of Histochemical Staining By Cationic Phthalocyanin Dyes;* The Design of Replacements for Alcian Blue, *J. Microscopy*, 119: 373-381 (1979) indicates that the commercially available Astra Blue free base (Bayer AG, Leverkusen, W. Ger.), shown as IIa below, can be methylated by dimethylsulfate to yield the quaternized (methylated Astra Blue, shown as IIb.

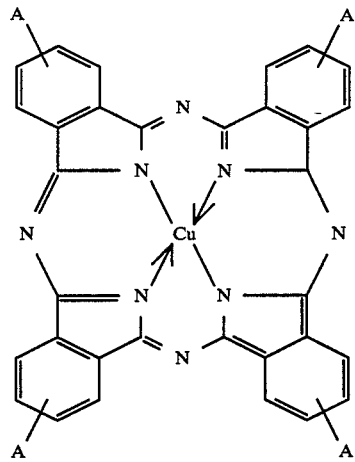

IIa: A = —SO$_2$—NH—(CH$_2$)$_3$—N(CH$_3$)$_2$

IIb: A = —SO$_2$—NH—(CH$_2$)$_3$—N$^+$(CH$_3$)$_3$

CH$_3$OSO$_3^-$

Although no use of these compounds in staining cellular or tissue materials was demonstrated by Scott, the desire to find compounds other than Alcian Blue for this purpose was expressed. This trimethyl quaternary salt and other phthalocyanin dyes were shown to stain polyanions such as heparin, polygalacturonate DNA and RNA. Thus, Scott teaches that these compounds do not selectively react with heparin as is required for differentiation of basophils.

In summary, Alcian Blue and Astra Blue free base have been the only compounds of this type which have been known to differentiate basophils from other white blood cells. The instability of Alcian Blue reagent has been a longstanding problem which has not been overcome. Thus, there remains the need for compounds which selectively stain basophils, in contrast to other white blood cells, and which are stable over time in solution.

SUMMARY OF THE INVENTION

The compounds of the present invention selectively associate with basophils and are stable in solution. They are useful in compositions which are particularly suitable for automated hematology systems in which strongly acidic reagents should be avoided. Such strongly acid reagents cause the degradation of polyester surfactants and further present a potential toxicity risk because they include cyanide which can be given off as toxic vapor.

The compounds to which the present invention relates have the structure:

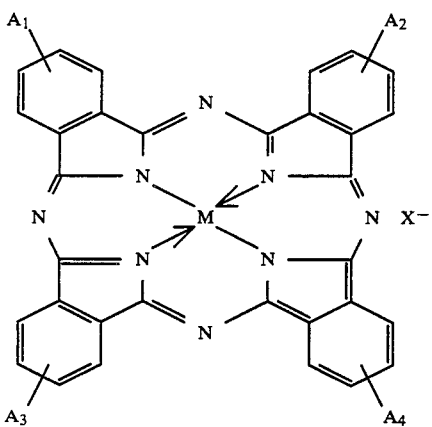

wherein $A_1$–$A_4$ is each independently hydrogen, sulfonate, or a $C_1$–$C_7$ hydrocarbon, optionally containing at least one heteroatom, with the proviso that at least one of $A_1$–$A_4$ is

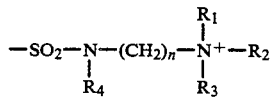

in which $R_1$–$R_3$ are each independently lower alkyls, cycloalkyls or olefins of which at least one is $C_2$–$C_4$ and two may join to form a ring; $R_4$ is hydrogen or a $C_1$–$C_3$ alkyl; n is an integer from 1 to 6; M is a polyvalent metal ion; and $X^-$ is a water soluble anion. It is preferred that at least two and especially at least three of $A_1$–$A_4$ have the structure so set forth. Most preferred of the above compounds are those in which at least one of $R_1$–$R_3$ is ethyl, propyl or allyl and in which n is 2 or 3.

The quaternized phthalocyanin compounds are provided by reacting Astra Blue free base with a substance comprising a water soluble anion and lower alkyls, cycloalkyls, or olefins of which at least one is $C_2$–$C_4$ and two may join to form a ring; and recovering the reaction product thereof. Preferably the water soluble anion is a bromide, chloride, iodide, or sulfate and the other component of the substance is a ethyl, propyl or allyl. Examples of the substance are n-propyl iodide, ethyl bromide, n-propyl bromide, n-butyl bromide and allyl bromide.

The quaternary ammonium ions described above are quite soluble in aqueous reagents over a wide pH range, e.g., 0.2–10, thereby avoiding the necessity of resorting to low pH ranges with its concomitant risk. These new compounds show excellent selectivity in staining basophils but not other blood cells as part of the composition herein described. Further, these compounds are stable in solutions which are used in selectively staining basophils, e.g., do not precipitate over long periods of time, e.g., three months at 45° C. This stability is particularly important in reagents for automated analysis apparatus.

The invention further provides a reagent composition incorporating at least the above compounds, lanthanum chloride and a surfactant effective to lyse red blood cells. Preferably it further comprises additional salts, such as sodium chloride. The composition stains basophils in preference to other blood cells with greater specificity and accuracy than Astra Blue or its quaternized methyl derivative. Performance compares favorably with the standard compound, Alcian Blue, as demonstrated by flow cytometry.

DESCRIPTION OF THE PREFERRED EMBODIMENTS

The compounds of the invention are phthalocyanin derivatives in which at least one of the aromatic rings are substituted. Preferably two or more of the rings are substituted in accordance with the invention by a moiety having the structure

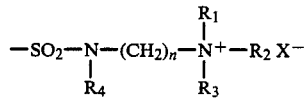

in which $R_1$–$R_3$ are each independently lower alkyls, cycloalkyls or olefins of which at least one is $C_2$–$C_4$ and two may join to form a ring. In the most preferred embodiments, at least one of $R_1$–$R_3$ is ethyl, propyl or allyl. Cyclopentylmethyl is also preferred. Two or more of $R_1$–$R_3$ can also be a $C_2$–$C_4$ alkyl, preferably ethyl or propyl. Where only one of $R_1$–$R_3$ is as described, it is preferred that the other two be identical. In this case they are usually methyl.

In any of the above embodiments, $R_4$ can be hydrogen or a $C_1$–$C_3$ alkyl. Preferably $R_4$ is hydrogen.

In the above structure, an alkylene moiety is positioned between the two nitrogens and can have n methylene units where n is an integer from 1 to 6. Preferably, n is 2 or 3.

The phthalocyanin ring structure is characterized by having a polyvalent metal ion bound in the center of the molecule. M is a polyvalent metal ion which is preferably selected from copper, nickel, zinc, cobalt, magnesium, iron, manganese or chromium.

The compounds of the invention are quaternized derivatives which, because of their positive charge, must exist in situ in the presence of $X^-$, a water soluble anion. Such anions are preferably bromide, chloride, iodide or sulfate.

Preferably, the ring substituents, other than those described by the above structure, are hydrogen, sulfonate, a linear or branched, saturated or unsaturated aliphatic or cycloliphatic hydrocarbon, an unsubstituted or substituted aryl or heteroaryl group, a benzyl radical or a benzyl substituted by oxygen or a non-alkylatable nitrogen or sulfur atom.

The above compounds are useful, in accordance with the invention, as dyes or stains which selectively color certain white blood cells (basophils) and not others. Human white blood cells can be classified into the categories of lymphocytes, monocytes and polymorphonucleocytes (PMNs). PMNs are granular and can be subclassified as neutrophils, eosinophils and basophils based on the staining characteristics of the cytoplasmic granules. These cell types and their relative populations in normal human blood can be summarized as follows:

| Cell Type | Percentage | Absolute Numbers (per ul) |
|---|---|---|
| Polymorphonuclear | | |
| Neutrophils | 40–75 | 2,500–7,500 |
| Eosinophils | 1–6 | 40–440 |
| Basophils | 1 | 15–100 |
| Monocytes | 2–10 | 200–800 |
| Lymphocytes | 20–45 | 1,500–3,500 |

This composition for the determination of basophils in a sample comprises, at least, a compound in accordance with the invention as described above, lanthanum chloride and a surfactant effective to lyse red blood cells.

Lanthanum chloride selectively inhibits the staining of nucleic acids. Preferred surfactants include cetyl pyridinium chloride and polyoxyethylene derivatives of unsaturated fatty acid esters of sorbitol, such as Tween 20 (I.C.I. United States, Inc., Wilmington, DE). Cetyl pyridinium chloride lyses red blood cells, eliminates undesired precipitates and prevents clumping of red cell membrane lysates.

This composition can optionally include alkali, metal salts such as sodium chloride, buffers and other non-critical components including those effective to establish a pH within a desired range.

The following working examples describe experiments which were performed in developing the present invention. Standard commercially available reagent grade chemicals were used whenever possible.

EXAMPLE I

Synthesis of Propyl Astra Blue Quaternary Ammonium Iodide

To prepare the quaternized propyl derivative of Astra Blue, 10.0 grams of Astra Blue 6 GLL free base (obtained from Mobay Chemical Co., Pittsburgh, PA) were added with stirring to 45 ml of dimethylformamide (DMF) in a 500 ml 3-necked round bottom flask. One neck was fitted with a reflux condenser having a $CaCl_2$ drying tube, another was fitted with a dropping funnel which contained 6.0 ml (10.5 g) of n-propyl iodide and 5.0 ml DMF, and the third neck was fitted with a ground glass stopper. After 10 minutes of stirring, the free base was completely dissolved and then the n-propyl iodide in DMF was added dropwise over a 20 minute period. The reaction flask was protected from light with an aluminum foil covering and the reaction mixture therein was stirred for 24 hours at room temperature (24°–26° C.). An aliquot was then removed and analyzed by paper chromatography along with a sample of free base in DMF, using a chromatography solution of (t-butanol:conc. $NH_4OH:H_2O$ (1:1:1) This procedure demonstrated that very little starting material ($R_f$ 1.0) remained. Blue products were found at $R_f$ 0.8 and 0.0 on the chromatogram.

The reaction mixture was then transferred to a 1-necked 500 ml round bottom flask. The 3-necked reaction flask was twice washed with 10 ml of water and the washings added to the 1-necked flask. The 1-necked flask was attached to a rotoevaporator and the water and excess n-propyl iodide were stripped at 40° C. with a water aspirator over a 15-minute period. The distillate so stripped was discarded. The emptied receiver flask was reattached to the rotoevaporator, surrounded by an ice water bath and the DMF was then stripped at 40° C. with a vacuum pump (0.1 mm Hg) over a 20-min. period to yield a blue solid. This solid was transferred to a 60 ml fritted-disc funnel and washed with 3×50 ml of diethyl ether in order to remove residual solvent and alkylating agent. The washed solid was dried by suction at 25° C. for 1 hr. Yield=15.0 grams.

Infrared Transmission

IR (KBr): Found=1155 and 1327 cm$^{-1}$ for

Required=1180-1140 cm$^{-1}$ and 1350-1300 cm$^{-1}$ for symmetrical and asymmetrical S-O stretch, respectively.

Ultraviolet Visible Spectrum

UV-VIS (DMF)-Deep blue Solution; max.(nm)

| λ max. | ε |
|---|---|
| 345 | 52,100 |
| 604 | 32,200 |
| 670 | 121,000 |

The observed spectrum is typical of metallophthalocyanins. See Sayer, et al, Accounts of Chemical Research, 15:73–79 (1982).

Elemental Analysis

Required for $C_{56}H_{73}N_{14}O_6S_3I_3Cu$, e.g., copper phthalocyanin $[SO_2NH(CH_2)_2N^+(CH_3)_2CH_2CH_2CH_3]_3I^-$ is: 42.6% C; 4.63% H; and 12.4% N. Found: 42.33%C; 4.54% H; and 13.22% N.

Syntheses of homologs were also conducted. Alkylations were performed as described above using Astra Blue 6 GLL free base and the following alkylating agents: methyl iodide, ethyl bromide, n-propyl bromide, n-butyl bromide, n-pentyl bromide, cyclopropylmethyl bromide, allyl bromide and benzyl chloride. The products obtained with both the bromides and iodides yielded analytical profiles similar to those reported above.

EXAMPLE II

Comparison of Basophil Reagents In Performance Testing

The basophil reagent composition used for testing in these experiments was prepared as follows. A 70 ml volume of deionized water was introduced into a 100 ml volumetric flask followed by 0.076 g of cetyl pyridinium chloride and this was stirred until completely dissolved. Then, 0.70 g $LaCl_3.6H_2O$ (lanthanum chloride), 0.90 g NaCl and 0.21 ml of Tween 20 were added and the mixture was stirred until they had completely dissolved. To this, 0.30 g of propyl Astra Blue 6 GLL quaternary ammonium bromide, prepared as described in Example I, was added, with stirring, until completely dissolved. Finally this mixture was brought to the mark with deionized water. This was then filtered through a 1 u filter.

Similarly, 100 ml portions of reagent comositions were also prepared, as above, using each of the alkylated derivatives of Astra Blue 6 GLL which were prepared by reaction of the free base with methyl iodide, ethyl bromide, n-butyl bromide, n-pentyl bromide, allyl bromide and benzyl chloride.

A reference reagent composition was prepared, as above, except that the dye added was Alcian Blue, 0.14 g/dl.

The absorbence at 610 nm of all of the above reagent solutions was determined by measuring the absorbence of a 100-fold dilution with water. As determined on a Beckman DU 7 spectrophotometer (Beckman Instruments, Inc., Fullerton, CA) with a 1 cm light path, the absorbence for each was the same, i.e. 40. Since all of these dyes, including Alcian Blue, possess the same Cu phthalocyanine chromophore, this procedure yielded reagents with the same molar concentration of dye for the comparison performance test, described below.

The reagent compositions prepared as described above were used in differential basophil testing as follows. Each of 10 whole blood samples was analyzed on a Technicon H-6000 hematology system (Technicon Instruments Corporation, Tarrytown, NY) in accordance with the manufacturer's instructions using the reference reagent composition. The instrument was put through a normal wash cycle and aliquots of the same 10 blood samples were then tested on it using the compositions containing the derivative components with intervening wash cycles. The mean percentage (Mean) of white blood cells which were basophils and the standard deviation (SD) of the 10 samples are reported in Table I.

mately two-fold; (2) the ethyl and propyl derivatives are, within the standard deviation, the same as that obtained by the reference reagent; (3) the butyl and pentyl derivatives overestimate the basophil count as compared to the ethyl, propyl and standard compounds but are still within that which can be accounted for by the standard deviation. However, the pentyl derivative rapidly began to produce a blue deposit on the instrument tubing, which would restrict flow and therefore performance. This did not occur with the other derivatives tested. In summary, this has demonstrated an unexpected and unpredictable performance of the ethyl and propyl derivatives, particularly as compared to the methyl derivatives.

The objectives of the experiments reported here were (1) to determine if the poor performance of the methyl derivatives was attributable to the presence of iodide counterion; and (2) to determine the comparative performance of the allyl derivative.

TABLE II

|   | Alcian Blue (Reference) | Propyl Astra Blue plus NaI(60 mg/dl) | Propyl Astra Blue Bromide | Allyl Astra Blue Bromide |
|---|---|---|---|---|
| 1 | 0.9 | 0.6 | 0.6 | 0.8 |
|   | 0.6 | 0.6 | 0.5 | 0.6 |
| 2 | 0.4 | 0.3 | 0.5 | 0.6 |
|   | 0.4 | 0.5 | 0.6 | 0.4 |
| 3 | 0.5 | 0.5 | 0.5 | 0.5 |
|   | 0.4 | 0.5 | 0.6 | 0.5 |
| 4 | 0.5 | 0.5 | 0.5 | 0.7 |
|   | 0.9 | 0.6 | 0.6 | 0.7 |
| 5 | 0.7 | 0.6 | 0.8 | 0.8 |
|   | 0.9 | 0.6 | 0.7 | 0.7 |
| Mean | 0.62 | 0.53 | 0.59 | 0.63 |
| SD | 0.21 | 0.09 | 0.09 | 0.13 |

These results indicate that (1) the quaternized allyl derivative performs in a manner equivalent to the quaternized propyl derivative and to Alcian Blue, and (2) the performance of the quaternized propyl derivative is not degraded by the presence of iodide ions. Hence, the poor performance of the methyl derivative is due to the methyl substitution, not to the presence of iodide counterions.

TABLE I

| Blood # | Alcian Blue (Reference) $X^- $ = chloride | Methyl AB $X^-$ = Iodide | Ethyl AB $X^-$ = bromide | n-Propyl AB $X^-$ = bromide | n-Butyl AB $X^-$ = bromide | N—Pentyl AB $X^-$ = bromide |
|---|---|---|---|---|---|---|
| 1 | 1.0 | 1.4 | 0.8 | 0.8 | 1.1 | 0.9 |
|   | 0.8 | 1.5 | 0.8 | 0.9 | 1.1 | 1.1 |
| 2 | 0.5 | 1.4 | 0.7 | 0.6 | 1.0 | 1.0 |
|   | 0.3 | 1.0 | 0.7 | 0.6 | 0.7 | 0.7 |
| 3 | 0.9 | 1.5 | 0.8 | 1.1 | 1.2 | 1.3 |
|   | 0.9 | 1.7 | 0.9 | 0.9 | 1.1 | 1.4 |
| 4 | 0.9 | 1.4 | 1.0 | 0.4 | 1.1 | 1.1 |
|   | 0.9 | 1.9 | 0.9 | 0.7 | 1.1 | 0.9 |
| 5 | 0.7 | 1.2 | 0.8 | 0.7 | 0.9 | 1.1 |
|   | 0.7 | 1.2 | 0.9 | 0.9 | 1.0 | 1.3 |
| 6 | 0.8 | 1.4 | 0.6 | 0.7 | 0.9 | 0.8 |
|   | 0.6 | 1.2 | 0.7 | 0.6 | 0.7 | 0.9 |
| 7 | 0.4 | 0.8 | 0.5 | 0.5 | 0.8 | 0.7 |
|   | 0.3 | 1.2 | 0.4 | 0.3 | 0.6 | 0.6 |
| 8 | 0.7 | 1.2 | 1.1 | 1.0 | 1.3 | 1.5 |
|   | 1.1 | 1.4 | 1.0 | 1.1 | 1.3 | 1.4 |
| 9 | 0.9 | 1.4 | 0.8 | 0.6 | 1.0 | 0.9 |
|   | 0.6 | 1.5 | 0.9 | 0.8 | 1.0 | 1.0 |
| 10 | 0.6 | 1.0 | 0.5 | 0.5 | 1.0 | 0.8 |
|   | 0.6 | 1.0 | 0.6 | 0.7 | 0.7 | 0.8 |
| Mean | 0.66 | 1.32 | 0.77 | 0.72 | 0.98 | 1.01 |
| SD | 0.24 | 0.26 | 0.18 | 0.22 | 0.20 | 0.26 |

The above data demonstrate that (1) the methyl derivative overestimates the basophil count by approxi-

EXAMPLE III

Stability of Baso Dye Reagent

The reagent tested in the experiments reported here was prepared as described in Example II, except that it contains 0.30 g/dl of propyl Astra Blue 6 GLL quaternary ammonium iodide. A drop of this reagent was placed on a clean glass slide and observed using a microscope at 200X magnification. The drop was free of observable particulate material. A 100 ml sample of this same reagent was stored for 7 weeks at 45° C. After storage, the reagent was found to still be free of particulates by microscopic examination at 200X and yielded performance data on a Technicon H-6000 system which was essentially the same as shown for propyl Astra Blue bromide in Table 1 and 1I.

What is claimed is:

1. A compound having the formula

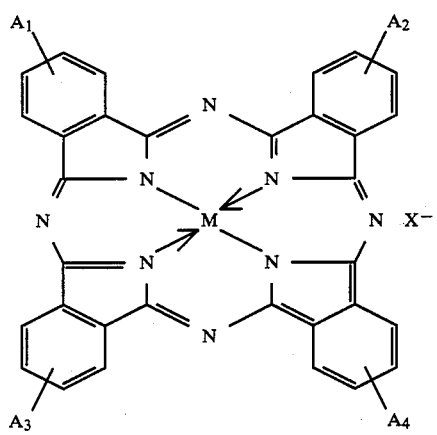

wherein each of $A_1$–$A_4$, same or different, is hydrogen, sulfonate, hydroxyl or a $C_1$–$C_7$ hydrocarbon, optionally containing at least one heteroatom, selected from alkoxy, cyano, carbalkoxy, a linear or branched, saturated or unsaturated aliphatic or cycloaliphatic hydrocarbon, an unsubstituted or substituted aryl or heteroaryl group, a benzyl radical or a benzyl substituted by oxygen or a nonalkylatable nitrogen or sulfur atom with the proviso that at least one of $A_1$–$A_4$ is

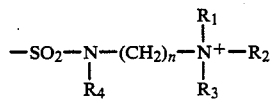

in which each of $R_1$–$R_3$, same or different, is lower alkyl, cycloalkyl or alkenyl, wherein at least one is $C_2$–$C_4$ and two of $R_1$–$R_3$ may join to form a ring; $R_4$ is hydrogen or a $C_1$–$C_3$ alkyl; n is an integer from 2 to 6; M is a polyvalent metal ion; and $X^-$ is a water-soluble anion.

2. The compound of claim 1 wherein at least two of $A_1$–$A_4$ are

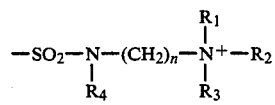

in which $R_1$–$R_3$ are each independently lower alkyls of which at least one is a $C_2$–$C_4$ alkyl; $R_4$ is hydrogen or a $C_1$–$C_3$ alkyl; n is an integer from 2 to 6; M is a polyvalent metal ion; and $X^-$ is a water soluble anion.

3. The compound of claim 1 wherein at least three of $A_1$–$A_4$ are

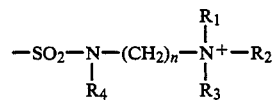

in which $R_1$–$R_3$ are each independently lower alkyls of which at least one is a $C_2$–$C_4$ alkyl; $R_4$ is hydrogen or a $C_1$–$C_3$ alkyl; n is an integer from 2 to 6; M is a polyvalent metal ion; and $X^-$ is a water soluble anion.

4. The compound of any one of claims 1, 2 or 3 wherein one of $R_1$–$R_3$ is $C_2$–$C_4$ and the other two are identical; $R_4$ is hydrogen; and n is 2 or 3.

5. The compound of any of claims 1, 2 or 3 wherein M is a polyvalent cation of copper, nickel, zinc, cobalt, magnesium, iron, manganese or chromium.

6. The compound of any of claims 1, 2 or 3 wherein $X^-$ is bromide, chloride, iodide or sulfate.

7. The compound of any of claims 1, 2 or 3 wherein at least one of $R_1$–$R_3$ is ethyl or propyl.

8. A compound of claim 1 in which $R_1$–$R_3$ are each independently lower alkyls of which at least one is ethyl, propyl or allyl and the other two are the same as each other; $R_4$ is hydrogen; n is 2 or 3; M is a polyvalent metal ion selected from cupric, nickel, zinc, cobalt, magnesium, ferric, ferrous, manganese or chromium; and $X^-$ is a water soluble anion selected from bromide, chloride, iodide or sulfate.

9. A composition for the determination of basophils in a sample, which composition comprises the compound of any of claims 1, 2, 3 or 8, lanthanum chloride and a surfactant effective to lyse red blood cells.

* * * * *